(12) United States Patent
Tinkl et al.

(10) Patent No.: US 6,417,357 B1
(45) Date of Patent: *Jul. 9, 2002

(54) COUPLING REACTIONS WITH PALLADIUM CATALYSTS

(75) Inventors: Michael Tinkl, Grenzach-Wyhlen (DE); Andreas Hafner, Gelterkinden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/646,206

(22) Filed: Sep. 14, 2000

(30) Foreign Application Priority Data

Mar. 18, 1998 (CH) .................................. 644/98

(51) Int. Cl.$^7$ .......................... C07C 43/20; C07F 15/00
(52) U.S. Cl. .................. 544/216; 564/337; 568/316; 568/323; 568/328; 568/331; 568/632; 568/642; 568/928; 585/427; 585/435
(58) Field of Search .................. 544/216; 564/337; 568/316, 323, 328, 331, 632, 642, 928; 585/427, 435, 438

(56) References Cited

U.S. PATENT DOCUMENTS

| | | | |
|---|---|---|---|
| 5,130,439 A | 7/1992 | Lo et al. | 548/110 |
| 5,559,277 A | 9/1996 | Beller et al. | 585/469 |
| 5,698,755 A | 12/1997 | Beller et al. | 585/466 |
| 5,831,107 A | 11/1998 | Beller et al. | 556/16 |
| 6,005,151 A | 12/1999 | Herrmann et al. | 585/438 |

FOREIGN PATENT DOCUMENTS

EP 0470795 2/1992

OTHER PUBLICATIONS

G. M. Direnzo, Journal of the Chemical Society, vol. 118, No. 26, (1996), pp. 6225–6234.
L. Hegedus et al., Journal of American Chemical Society, vol. 104, No. 3, (1982), pp. 697–704.
M. Uemura et al., Tetrahedron Letters, vol. 34, No. 1, (1993), pp. 107–110.
M. Uemura et al., Journal of Organometallic Chemistry, 473, (1994), pp. 129–137.
T. Wallow et al., J. Org. Chem., (1994), 59, pp. 5034–5037.
A. F. Indolese, Tetrahedron Letters, vol. 38, No. 20, pp. 3513–3516 (1997).
Y. Inoue et al., Synthesis, 3, (1984), p. 244.
B. Akermark et al., Organometallics, vol. 6, No. 1, (1987), pp 620–628.
J. Powell et al., Inorg. Phys. Theor., Journal of the Chemical Society Section A (1967), pp. 1839–1851.
M. Kawatsura et al., Chem. Commun., No. 2, (1998), pp. 217–218.

*Primary Examiner*—Richard L. Raymond
(74) *Attorney, Agent, or Firm*—Kevin T. Mansfield

(57) ABSTRACT

This invention relates to a novel, inventive process for the preparation of biphenyls or aromatic olefins by coupling reactions of the Suzuki coupling and Heck coupling type, using allylpalladium catalysts of the $\mu$-halo (triisopropylphosphine)($\eta^3$-allyl)palladium(II) type.

9 Claims, No Drawings

COUPLING REACTIONS WITH PALLADIUM CATALYSTS

This application is a 371 of PCT/EP99/01474, filed Mar. 8, 1999.

The present invention relates to a novel, inventive process for the preparation of biphenyls or aromatic olefins by coupling reactions using allyl palladium catalysts and novel allyl palladium catalysts.

Biphenyls and aromatic olefins can have versatile uses as chemical specialities for the preparation of liquid crystals, as photoinitiators, UV absorbers, fluorescent whitening agents, ligands for catalysts and as starting materials for the preparation of intermediates for agro-chemicals and pharmaceutical products.

A frequently used method for the synthesis of biphenyls is the palladium-catalysed cross-coupling (so-called Suzuki coupling) in which iodine aromatic compounds or bromine aromatic compounds or arylsulfonates are reacted with arylboron derivatives in the presence of palladium catalysts. This method is described, inter alia, in N. Miyaura et al., *Synthetic Communications*, 11 (1981), 513; A. Suzuki in Metal-catalyzed Cross-coupling Reactions, chapter 2, Wiley—VCH, Weinheim 1998, in U.S. Pat. No. 5,130,439 and in EP-A-470 795.

A frequently used method for the synthesis of aromatic olefins is the palladium-catalysed coupling reaction, the socalled Heck reaction, in which iodine aromatic compounds or bromine aromatic compounds are reacted with olefins in the presence of palladium catalysts. This method is described, inter alia, in R. F. Heck, acc. *Chem. Res.* 1979, 12, 146; R. F. Heck, *Org. React.* 1982, 27, 345; and in R. F. Heck, *Palladium Reactions in Synthesis*, Academic Press, London 1985, S. Bräse and A. De Meijere in Metal-catalyzed Cross-coupling Reactions, chapter 3, Wiley—VCH, DE-Weinheim 1998.

In spite of their interesting broad utility, these methods have drawbacks regarding the synthesis. For example, if one does not want to use the catalyst in amounts of more than 1 mol %, then only small amounts of product can be produced on a laboratory scale by the cited coupling reactions. In the Suzuki reaction, the use of conventional palladium catalysts, e.g. Pd(PPh$_3$)$_4$, Pd(OAc)$_2$ and triphenyl phosphine, results in undesirable side reactions through aryl transference from the catalyst to the substrate; D. F. O'Keefe et al. *Tetrahedron Left.*, 1992, 6679. The recovery of the palladium catalyst is elaborate in the case of the cited coupling reactions, the separation of the palladium residue from the reaction mixture requiring first the conversion of that residue into a palladium salt, e.g. palladium chloride or palladium acetate.

It is the object of this invention to find suitable catalysts for coupling reactions of biphenyls of the Suzuki cross-coupling type and of aromatic olefins of the Heck coupling type which promise improved turnover numbers (mol product/mol catalyst) and enhanced reactivity and selectivity over the catalysts used in such coupling reactions.

This object is achieved by the present invention which provides a novel, inventive process for the preparation of biphenyls and aromatic olefins using olefinic palladium complex compounds.

This invention relates to a process for the preparation of biphenyls of formula

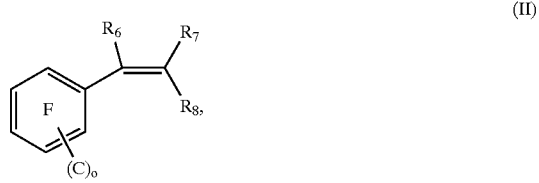

wherein A and B define substituents; m and n define integers from 0 to 5 and the number of substituents at the phenyl radicals D and E; or
of aromatic olefins of formula

wherein C defines substituents, o defines integers from 0 to 5 as well as the number of substituents at the phenyl radical F, and R$_6$, R$_7$ and R$_8$ are hydrogen or substituents, which process comprises
a) subjecting a phenyl derivative of formula

wherein A, B, m and n have the meanings cited for formula I and X is a leaving group, for the preparation of the biphenyls (I) to a coupling reaction with an arylboronic acid derivative of formula

wherein A, B, m and n have the meanings cited for formula I and Y is the—B(OH)$_2$ group or mono- or diester derivatives of—B(OH)$_2$; and
b) subjecting a phenyl derivative of formula

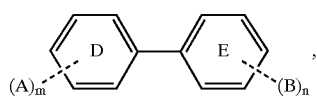

wherein C and o have the meanings cited for formula II and X is a leaving group, for the preparation of the aromatic olefins (II) to a coupling reaction with an olefin of formula

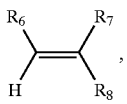

(VI)

wherein $R_6$, $R_7$ and $R_8$ have the meanings cited for formula 11, each in the presence of a catalytically effective amount of an olefinic palladium complex compound of formula

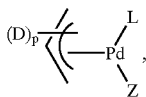

(VII a)

wherein L is a neutral ligand having electron-donor properties, Z is an anionic ligand and D is a substituent, and p is an integer from 0 to 5 and defines the number of substituents at the allyl group; or a') subjecting a phenyl derivative (III a) or (IIIb), wherein A, B, m and n have the meanings cited for formula I and X is chloro, bromo or iodo, for the preparation of the biphenyls (I) to a coupling reaction with an arylboronic acid derivative (IV a) or (IV b), wherein A, B, m and n have the meanings cited for formula I and Y is the—B(OH)$_2$ group or mono- or diester derivatives of—B(OH)$_2$; or b') subjecting a phenyl derivative (V), wherein C and o have the meanings cited for formula II and X is bromo or iodo, for the preparation of the aromatic olefins (II) to a coupling reaction with an olefin (VI), wherein $R_6$, $R_7$ and $R_8$ have the meanings cited for formula II, in the presence of a catalytically effective amount of an olefinic, ionic palladium complex compound of formula

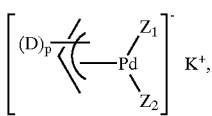

(VIIb)

wherein $Z_1$ and $Z_2$ are anionic ligands and $K^+$ is a non-coordinating cation and D and p have the cited meanings, and isolating the biphenyl (I) or the condensed aromatic olefin (II) after the completion of the process variants a), b), a') or b').

The catalysts used in this process can be easily obtained by simple synthesis, for example by the method of B. Akermark et al., *Organometallics* 1987, 6, 620–628, and have substantially improved reactivity and selectivity. After the reaction is complete, the dissolved olefinic palladium complex compounds can be degraded to palladium black using atmospheric oxygen. Using the method of Y. Inoue et al. *Synthesis* 1984, 3, 244, this residue can be used again directly for the catalyst synthesis without any detour over the conversion into a palladium salt, such as palladium chloride or palladium acetate.

The terms and denotations used in this description of the invention preferably have the following meanings:

Biphenyls (I) are preferably substituted at the phenyl ring D by 1 to 5 substituents from the group A containing the substituents $R_1$, $R_2$, $R_3$, $R_4$ and $R_5$, and at the phenyl ring E also preferably by 1 to 5 substituents from the group B containing the substituents from the group $R_6$, $R_7$, $R_8$, $R_9$ and $R_{10}$. Suitable substituents are listed in the List of Radical Names, which is valid according to IUPAC Rules, and remain unchanged under the conditions of the coupling reactions. Any of the substituents may be selected. Suitable substituents A from the group $R_1$, $R_2$, $R_3$, $R_4$ and $R_5$ are selected, for example, from the group consisting of the functional groups or derivatised functional groups consisting of amino, $C_1$–$C_4$alkylamino, $C_1$–$C_4$dialkylamino, hydroxy, oxo, thio, -NO$_2$, carboxy, carbamoyl, sulfo, sulfamoyl, ammonio, amidino, cyano, formylamino, formamido and halogen, or are saturated or unsaturated aliphatic, cycloaliphafic or heterocycloaliphatic radicals, carbocyclic or heterocyclic aryl radicals, condensed carbocyclic, heterocyclic or carbocyclic-heterocyclic radicals, which may in turn be combined with any others of these radicals and which may be substituted by the cited functional groups or derivatised functional groups.

The cited substituents and radicals can additionally be interrupted by one or more than one bivalent radical selected from the group consisting of —O—, —S—, —C (=O)—O—, —O—C(=O)—, —(=O)—N ($C_1$-$C_4$alkyl)—, —N($C_1$-$C_4$alkyl)—C(=O)—, —S(=O)—, —S(=O)$_2$—, —S(=O)—O—,—S(=O)$_2$—O—, —O—S(=O)—, —O—S(=O)$_2$—, —S(=O)—N($C_1$-$C_4$alkyl)—, —S(=O)$_2$—N($C_1$-$C_4$alkyl)—, —($C_1$-$C_4$alkyl)N—S (=O)—, —($C_1$-$C_4$alkyl)N—S(=O)$_2$—, —P(=O)—, —P(=O)—O—, —O—P(=O)— and —O—P(=O)—O—.

Two substituents from the group $R_1$, $R_2$, $R_3$, $R_4$ and $R_5$ can also be bivalent, bridge-like $C_2$–$C_6$alkylene, $C_4$–$C_8$alkyldiylidene or $C_4$–$C_8$alkenyldiylidene groups, preferably butanediylidene, more preferably 2-butenediylidene, which are bound to the phenyl ring D or to the heteroaryl substituent A, e.g. pyridyl, or which are condensed to an aromatic bicycle, which can likewise be substituted by the cited functional groups or substituents.

Suitable substituents B from the group $R_6$, $R_7$, $R_8$, $R_9$ and $R_{10}$ have the meanings cited for $R_1$ to $R_5$ and can also be substituted by further substituents. $R_1$, $R_2$, $R_3$, $R_4$ and $R_5$ and $R_6$, $R_7$, $R_8$, $R_9$ and $R_{10}$ are defined each independently of one another.

Suitable substituents A from the group $R_1$, $R_2$, $R_3$, $R_4$ and $R_5$ are preferably functional groups from the group consisting of amino, $C_1$–$C_4$alkylamino, for example methylamino or ethylamino, $C_1$–$C_4$dialkylamino, for example dimethylamino or diethylamino, hydroxy, oxo, thio, —NO$_2$, carboxy and halogen, or are substituents from the group $C_1$–$C_{20}$alkyl, $C_2$—$C_{20}$alkenyl, $C_2$–$C_{20}$alkynyl, $C_3$–$C_{12}$cycloalkyl, $C_7$-$C_{12}$bicycloalkyl, $C_4$-$C_{12}$cycloalkenyl, $C_2$–$C_{11}$heterocycloalkyl, carbocyclic $C_6$–$C_{16}$aryl, $C_2$–$C_{15}$heteroaryl, carbocyclic $C_7$–$C_{16}$aralkyl and $C_2$–$C_{15}$heteroarylalkyl, which can in turn be substituted by the cited functional groups and which can be interrupted by bivalent radicals.

$C_1$–$C_{20}$Alkyl is, for example, methyl, ethyl, n- or isopropyl or n-, sec- or tert-butyl and also straight-chain or branched pentyl, hexyl, heptyl, octyl, isooctyl, nonyl, tert-nonyl, decyl, undecyl or dodecyl.

$C_2$–$C_{20}$Alkenyl is, for example, vinyl, allyl, 2-or 3-butenyl, isobutenyl or n-penta-2,4-dienyl.

$C_2$–$C_{20}$Alkynyl is, for example, 1- or 2-propynyl.

$C_3$–$C_{12}$Cycloalkyl is, for example, cyclopropyl, dimethylcyclopropyl, cyclobutyl, cyclopentyl or cyclohexyl.

$C_7$–$C_{12}$Bicycloalkyl is, for example, bornyl or norbornyl.

$C_4$–$C_{12}$Cycloalkenyl is, for example, cyclopentadienyi or cyclohexenyl.

$C_2$–$C_{11}$Heterocycloalkyl preferably contains 4 or 5 carbon atoms and one or two heteroatoms from the group O, S and N. Examples are the substituents derived from oxirane, azirine, 1,2-oxathiolane, pyrazoline, pyrrolidine, piperidine, piperazine, morpholine, tetrahydrofuran or tetrahydrothiophene.

Carbocyclic $C_6$–$C_{16}$aryl is, for example, mono-, bi- or tricyclic, typically phenyl, naphthyl, indenyl, azulenyl or anthryl.

$C_2$–$C_{15}$Heteroaryl is preferably monocyclic or is condensed with another heterocycle or with an aryl radical, e.g. phenyl, and preferably contains one or two, in the case of nitrogen up to four, heteroatoms selected from the group consisting of O, S and N. Suitable substituents are derived from furan, thiophene, pyrrole, pyridine, bipyridine, picolylimine, γ-pyrane, γ-thiopyrane, phenanthroline, pyrimidine, bipyrimidine, pyrazine, indole, coumarone, thionaph thene, carbazole, dibenzofuran, dibenzothiophene, pyrazole, omidazole, benzimidazole, oxazole, thiazole, dithiazole, isoxazole, isothiazole, quinoline, isoquinoline, acridine, chro mene, phonazine, phenoxazine, phenothiazine, triazine, thianthrene, purine or tetrazole.

Carbocyclic $C_7$–$C_{16}$aralkyl preferably contains 7 to 12 carbon atoms, for example benzyl, 1- or 2-phenethyl or cinnamyl.

$C_2$–$C_{15}$leteroarylalkyl preferably consists of the cited heterocycles which substitute e.g. $C_1$–$C_4$alkyl radicals, depending on the length of the carbon chain where possible terminally or else also in adjacent position (1-position) or in α-position (2-position).

In an aromatic olefin of formula II, the index o preferably means 1 to 5. The phenyl ring F is preferably substituted by 1 to 5 substituents C from the group containing the substituents $R_1$, $R_2$, $R_3$, $R_4$ and $R_5$ which are as defined above under formula I for A and $R_1$ to $R_5$. In the olefinic side chains, $R_6$, $R_7$ and $R_8$ are hydrogen or substituents which are also as defined above under formula I for A and $R_1$ to $R_5$.

In the phenyl derivative of formula III a or III b used in accordance with process variant a), X is a leaving group which is expelled during the coupling reaction, the so-called Suzuki cross-coupling. This reaction type is illustrated by the following reaction for the preparation of a photoinitiator.

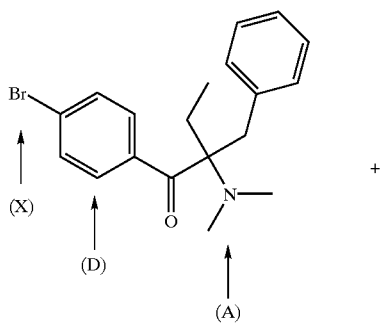

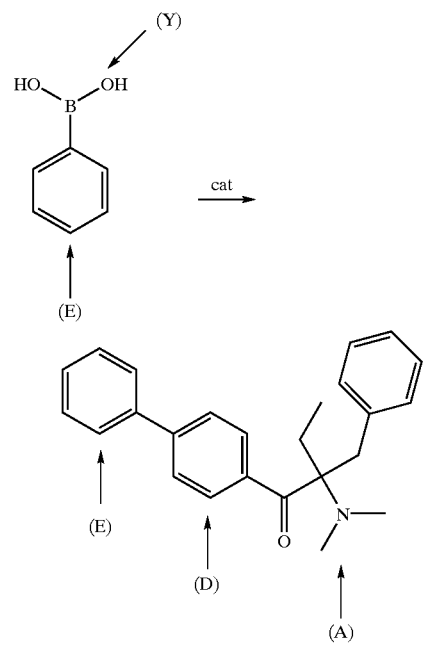

A suitable leaving group X is known e.g. for the coupling reactions of the Suzuki type and is, for example, halogen, e.g. chloro, bromo or iodo, or an organosulfonyl radical, e.g. mesyl, p-toluenesulfonyl or trifluoromethanesulfonate. It has been found that chlorine is suitable as leaving group when the catalysts (VII a) are used. Otherwise, coupling reactions of the Suzuki type proceed with satisfactory yield and TON only when higher halogens, e.g. bromo or iodo, are used as leaving group. The above process is the first palladium catalyst-mediated coupling of a deactivated (by electron-rich or electron-shifting groups), substituted aryl chloride by the Suzuki method.

In a special process variant, the substituents A (m=1) or B (n=1) in a phenyl derivative of formula III a or III b can also be an additional leaving group X having the cited meanings. The phenyl derivative (III a, III b) concerned contains in this case two leaving groups X. It is possible to couple such a derivative with two equivalents of arylboronic acid derivatives of formula IV a or IV b so that a phenyl ring E is combined with two phenyl rings D in the process product which can be thus obtained. In analogy, products are obtained wherein one phenyl ring D is combined with two phenyl rings E.

In another process variant, it is possible that the substituents A and B in phenyl derivatives of formula III a or III b also contain additional leaving groups X. The phenyl derivative (III a, III b) concerned contains in this case two or more leaving groups X. Such a derivative can be coupled with corresponding equivalent arylboronic acid derivatives of formula IV a or IV b so that the phenyl rings D or E in the process product which can be thus obtained are additionally coupled to the substituents A or B with further phenyl rings D or E. This process variant is illustrated by the following coupling reaction:

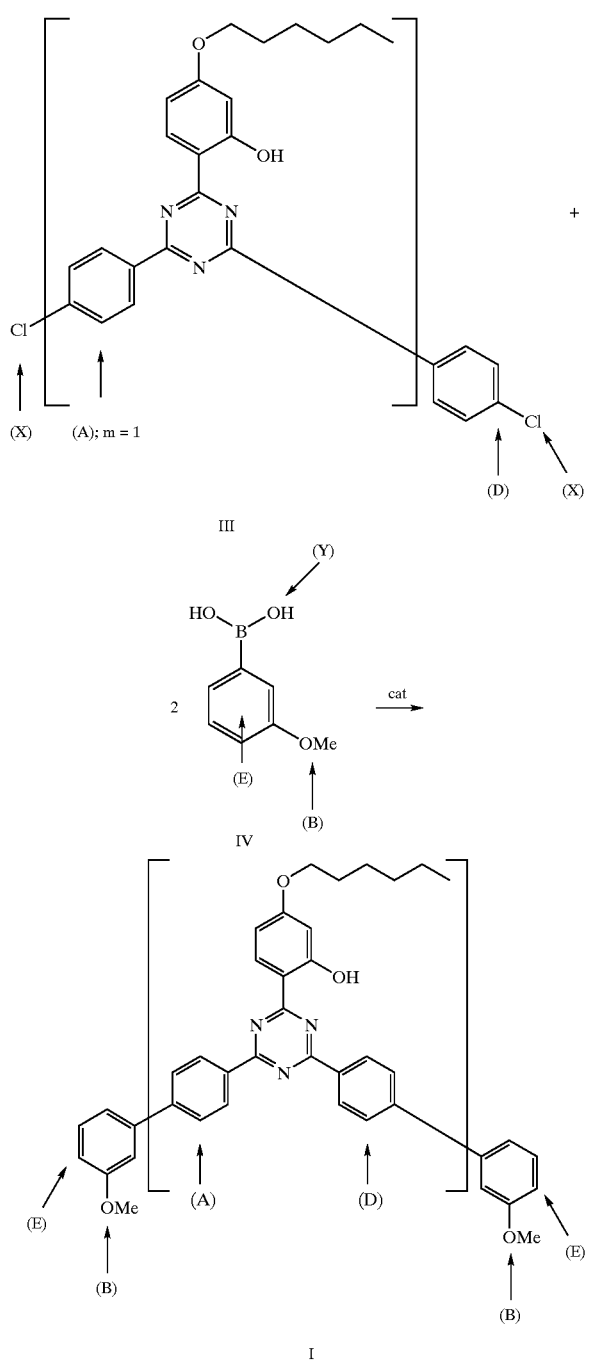

wherein cat. (above the reactions arrow) signifies the catalyst (VII a).

In the arylboronic acid derivatives of formulae IV a and IV b used in accordance with process variant a), Y is also a leaving group defined as —B(OH)$_2$ or mono- or diester derivatives of —B(OH)$_2$. Mono- or diester derivatives of —B(OH)$_2$ are, for example, —B(O—C$_1$–C$_4$alk)$_2$ or —BOH—C$_1$–C$_4$alk, where C$_1$–C$_4$alk is preferably methyl or ethyl, —B(O—Ar)$_2$ or —BOH—Ar, where Ar is preferably aryl.

In the phenyl derivative (V) used according to process variant b), the index o and the substituents C have the meanings cited for formula II. A suitable leaving group X is known, for example, for the Heck type coupling reactions and is typically halogen, e.g. bromo or iodo.

In an olefinic palladium complex compound of formula VII a, L is a neutral ligand having electron-donor properties. Suitable ligands are, for example, phosphine ligands of the tertiary phosphine type.

A suitable tertiary phosphine preferably contains 3 to 40, more preferably 3 to 18, carbon atoms and preferably conforms to formula:

$$PR^1R^2R^3 \quad (VIII),$$

wherein $R^1$, $R^2$ and $R^3$ are each independently of one another C$_1$–C$_{20}$alkyl, C$_4$–C$_{12}$cycloalkyl, C$_2$–C$_{11}$heterocycloalkyl, C$_6$–C$_{16}$aryl, C$_7$–C$_{16}$aralkyl or C$_2$–C$_{15}$heteroarylalkyl having the meanings cited above, which radicals may be substituted by substituents selected from the group consisting of C$_1$–C$_6$alkyl, C$_1$–C$_6$alkoxy, C$_1$–C$_6$haloalkyl, C$_6$–C$_{16}$aryl, —NO$_2$, SO$_3$, ammonium and halogen. $R^1$ and $R^2$ together can be tetra- or pentamethylene which is unsubstituted or substituted by C$_{1-6}$alkyl, C$_1$–C$_6$haloalkyl, —NO$_2$ or C$_1$–C$_6$alkoxy which are condensed with 1 or 2 bivalent 1,2-phenylene radicals, $R^3$ having the meaning cited above.

Also preferred are sterically exacting radicals $R^1$, $R^2$ and $R^3$, for example cyclic or branched, particularly preferably α,α-dibranched and, very particularly preferably α-branched, alkyl groups.

Particularly preferred are those compounds (VII), wherein $R^1$, $R^2$ and $R^3$ are methyl, ethyl, n- or i-propyl, n-, i-, s- or t-butyl, 1-, 2- or 3-pentyl, 1-, 2-, 3- or 4-hexyl, cyclopentyl, cyclohexyl, phenyl, naphthyl or benzyl, for example (i-C$_3$H$_7$)$_3$P, (C$_5$H$_9$)$_3$P and (C$_6$H$_{11}$)$_3$P.

An anionic ligand is, for example, the hydride ion (H$^-$) or a ligand which is derived, for example, from inorganic or organic acids by the splitting off of protons, e.g. a halide (F$^-$, Cl$^-$, Br$^-$ and I$^-$) or anions of oxygen acids or derivatives thereof, for example SnCl$_3^-$, SnCl$_5^-$, BF$_4^-$, B(aryl)$_4^-$, PF$_6^-$, SbF$_6^-$ or AsF$_6^-$.

Anions of oxygen acids are, for example, sulfate, phosphate, perchlorate, perbromate, periodate, antimonate, arsenate, nitrate, carbonate, the anion of a C$_1$–C$_8$acarboxylic acid, for example formiate, acetate, propionate, butyrate, benzoate, phenylacetate, mono-, di- or trichloro- or fluoroacetate, sulfonates, for example mesylate, ethanesulfonate, propanesulfonate, n-butanesulfonate, trifluoromethanesulfonate (triflate); benzenesulfonate or p-toluenesulfonate which are unsubstituted or substituted by C$_1$–C$_4$alkyl, C$_1$–C$_4$alkoxy or halogen, in particular by fluoro, chloro or bromo, for example benzenesulfonate, tosylate, p-methoxy or p-ethoxybenzenesulfonate, pentafluorobenzenesulfonate or 2,4,6-triisopropylbenzenesulfonate.

Particularly preferred anionic ligands are H$^-$, F$^-$, Cl$^-$, Br$^-$, BF$_4^-$, PF$_6^-$, SnCl$_3^-$, SbF$_6^-$, AsF$_6^-$, CF$_3$SO$_3^{31}$, C$_6$H$_5$-SO$_3^-$, 4-methyl-C$_6$H$_5$-SO$_3^-$, 3,5-dimethyl-C$_6$H$_5$-SO$_3^-$, 2,4,6-trimethyl-C$_6$H$_5$-SO$_3^-$ and 4-CF$_3$-C$_6$H$_5$-SO$_3^-$ and also cyclopentadienyl (Cp$^-$). Cl$^-$, Br$^-$, or I$^-$ are particularly preferred.

Suitable substituents D remain unchanged under the conditions of the coupling reactions. Any substituents may be chosen. Suitable substtuents D are selected from the group consisting of R$_1$, R$_2$, R$_3$, R$_4$ and R$_5$. Index p is preferably 1 and 2. Suitable substituents are typically selected from the group consisting of hydroxy, halogen, e.g. chloro, carboxy and esterified carboxy, e.g. methoxy- or ethoxycarbonyl, or are saturated or unsaturated aliphatic, cycloaliphatic or heterocycloaliphatic radicals, carbocyclic or heterocyclic aryl radicals, condensed carbocyclic, heterocyclic or carbocyclic-heterocyclic radicals or suitable combinations of these radicals, which may in turn be substituted by one or more than one substituent from the group consisting of hydroxy, halogen, oxo, esterified carboxy, e.g. ethoxy- or methoxycarbonyl, and acyl, e.g. acetyl.

Suitable olefinic palladium complex compounds (VII a) containing substituents at the allyl group are represented by the following structural formulae:

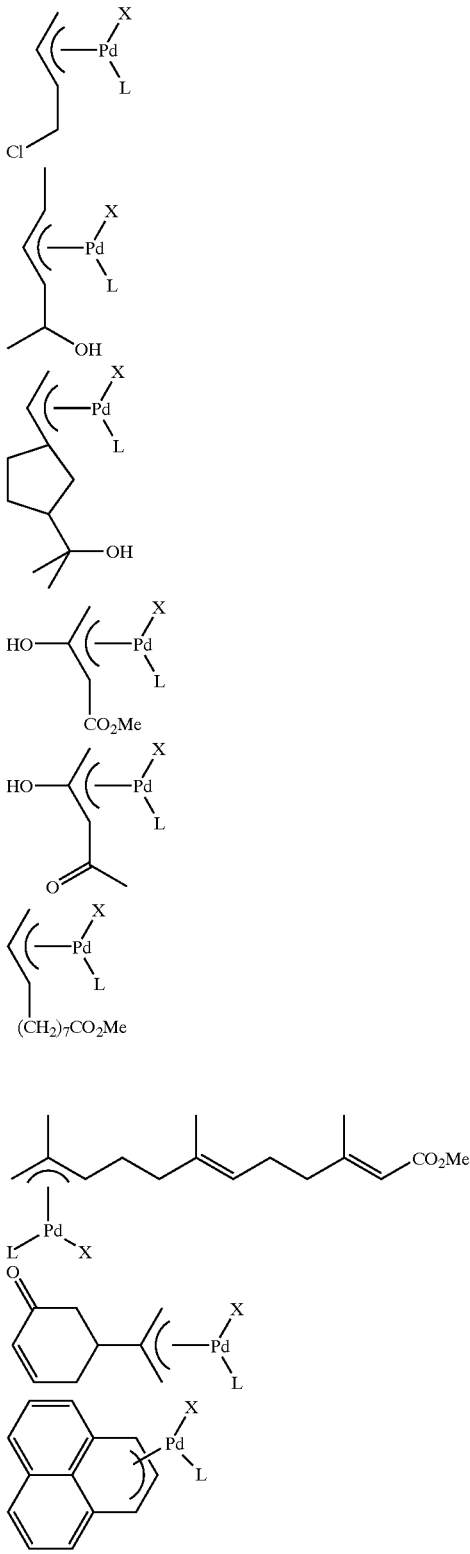

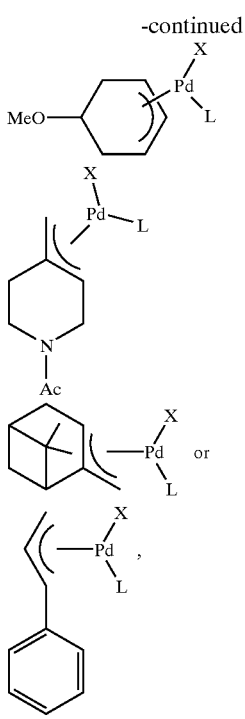

wherein X and L have the cited meanings and are preferably tricyclohexylphosphine or triisopropylcyclophosphine and halogen, typically chloro, bromo or iodo.

The substituents of the allyl group can also be combined to polynuclear bridged complexes in the sense of the following structure:

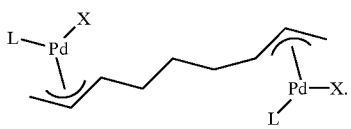

Preferred olefinic palladium complex compounds (VII a) are those containing no subsbtuents at the allyl group which is bound to palladium (index p is 0), L is the tricyclohexylphospine or triisopropylcyclophosphine group and X is halogen, typically chloro, bromo or iodo.

In an olefinic ionic palladium complex compound of formula VII b, D and p have the meanings cited above for compounds of formula VII a. The index p is preferably 0. The meanings of the anionic ligands of $Z_1$ and $Z_2$ correspond to the meaning of Z. $Z_1$ and $Z_2$ are preferably halogen, typically chloro, bromo or iodo. The non-coordinating cation $K^+$ is voluminous and corresponds in size to the palladium complex anion which carries a negative charge because of the presence of the second anionic ligand $Z_2$. A preferred non-coordinating cation $K^+$ is, for example, the tetraphenylphosphonium cation.

The reaction conditions for the coupling reactions are described in the literature and correspond to the reaction conditions known for the so-called Suzuki coupling and Heck coupling reactions.

The process of this invention is preferably carried out such that the reactants can be reacted with each other in any order. Preferably, the phenyl derivatives with the leaving groups X, i.e. compounds of formula III a or III b, or compounds V, are placed first in a vessel and then the arylboronic acid derivatives of formula IV a or IV b or the olefin compound (VI) are added.

In the sense of a cross-coupling, the phenyl rings D and E can be combined to the combination D with E by using the starting materials III a and IV a, to the combination D with D by using the starting materials III a and IV b to the combination E with E by using the starting materials III b and IV a, and to the combination E with D by using the starting materials III b and IV b.

The term catalytic amounts preferably means amounts of about 0.0001–5.0 mol %, more preferably of 0.001–1.0 mol %, based on the amount of the substrate used.

The molar ratio of the reactants of the coupling reactions of the compounds of formula III a or III b to the arylboronic acid derivatives of formula IV a or IV b, or of the compounds (V) to the olefin compound (VI), is usually in the range from 1:1 to 1:10, the preferred ratio being in the range from 1:1 to 1:2. The reaction is carried out at temperatures up to the boiling temperature of the solvent, preferably at room temperature up to the boiling temperature of the solvent (reflux conditions). Suitable solvents are customary, preferably higher-boiling, solvents, for example non-polar aprotic solvents, e.g. xylene or toluene, or polar aprotic solvents, e.g. dimethylformamide. The obtainable reaction product (I) or (II) is worked up and isolated in a manner known per se by conventional purification processes, for example after removal of the solvent and subsequent separation processes, such as precision distillation, recrystallisation, preparative thin-layer chromatography, column chromatography, preparative gas chromatography and the like.

A particular embodiment of the process comprises a) subjecting a phenyl derivative (III) for the preparation of the biphenyls (I) to a coupling reaction with an arylboronic acid derivative (IV); or b) subjecting a phenyl derivative (V) for the preparation of the aromatic olefin (II) to a coupling reaction with an olefin (VI), each in the presence of an olefinic palladium complex compound (VII a), wherein L is a neutral ligand having electron-donor properties, Z is halogen and p is 0, or in the presence of an olefinic ionic palladium complex compound (VII b), wherein $Z_1$ and $Z_2$ are halogen, $K^+$ is the tetraphenylphosphonium cation and p is 0 and, after carrying out the process variants a) or b), isolating the biphenyls (I) or the condensed aromatic olefin (II).

In a particularly preferred process variant, each of the coupling reactions are carried out in the presence of an olefinic palladium complex compound (VII a), wherein L is triisopropylphosphine or tricyclohexylphosphine, Z is halogen, typically chloro, bromo or iodo, and p is 0.

This invention also relates to olefinic palladium complex compounds of formula

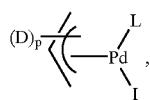

(VII'a)

wherein L is a neutral ligand having electron-donor properties, I is iodine and D is substituents, and p is an integer from 0 to 5 and defines the number of the substituents at the allyl group.

A particularly preferred subject matter of this invention are palladium complex compounds of formula

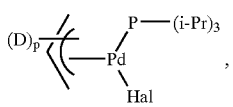

(VII"a)

wherein i-Pr is isopropyl, Hal is chloro or bromo and D is substituents, and p is an integer from 0 to 5 and defines the number of substituents at the allyl group, and also olefinic complex compounds of formula

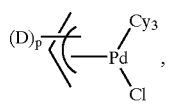

(VII'''a)

wherein Cy is cyclohexyl, Cl is chloro and D is substituents, and p is an integer from 0 to 5 and defines the number of substituents at the allyl group.

A particularly preferred subject matter of this invention are the compounds of formulae

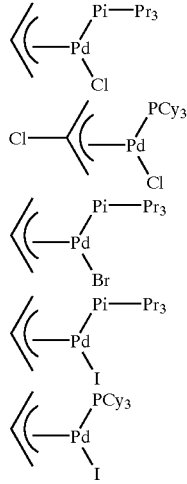

The preparation of such olefinic palladium complex compounds, which are a subject matter of this invention, and of the known palladium complex compounds is carried out in a manner known per se by reacting a known dimeric allyl-halo-palladium complex with a compound introducing the ligand L, for example with triisopropyl- or tricyclohexylphosphine:

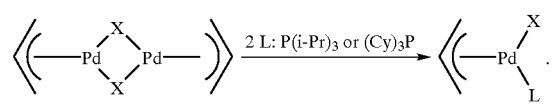

This reaction can be carried out in analogy to the method according to B.Åkermark et al., *Organometallics* 1987, 6, 620–628 or Y.Hayashi et al. *J.Chem. Soc. Dalton Trans.* 1989, 1519.

This invention also relates to the process for the preparation of the novel olefinic palladium complex compounds (VII a).

The preparation of the dimeric allyl-halopalladium complexes is known and is described, inter alia, in Y.Tatsuno et al., *Inorg. Synth.* 1979, 14, 220; Y.Inoue et al. *Synthesis*, 1984, 3, 244; B. M. Trost et al. *J. Amer. Chem. Soc.* 1980, 102, 3572.

Olefinic ionic palladium complex compounds of formula VII b are known. Their preparation is described in R. J. Goodfellow et al., *J. Chem. Soc.* (A), 1966, 784.

The use of olefinic palladium complex compounds of formula VII a and of the olefinic ionic palladium complex compounds of formula VII b for the catalysis of coupling reactions of aromatic compounds with each other and of aromatic compounds with olefins is, in principle, novel and inventive. Accordingly, the use according to this invention relates both to known and to novel compounds which are covered by formulae VII a and VII b.

In another of its aspects, this invention relates to the use of an olefinic palladium complex compound of formula

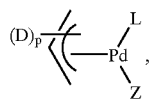
(VII a)

wherein L is a neutral ligand having electron-donor properties, Z is an anionic ligand and D is substituents, and p is an integer from 0 to 5 and defines the number of substituents at the allyl group, and to the use of an olefinic ionic palladium complex compound of formula

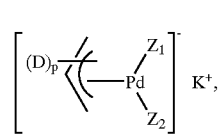
(VIIb)

wherein $Z_1$ and $Z_2$ are anionic ligands, $K^+$ is a complex-stabilising cation and D is substituents, and p is an integer from 0 to 5 and defines the number of substituents at the allyl group, for the catalytic preparation of biphenyls or olefinic aromatic compounds by coupling reactions.

A preferred subject matter of this invention is the use of olefinic palladium complex compounds of formula VII a and of the olefinic ionic palladium complex compounds of formula VII b for the catalysis of coupling reactions in the sense of the Suzuki coupling of aromatic compounds and of the Heck coupling of aromatic compounds with olefins.

The following Examples illustrate the invention:

EXAMPLES

A Suzuki Coupling

Table 1 illustrates syntheses according to the method of the Suzuki coupling (method X1: coupling of aryl bromides; method X2: coupling of aryl chlorides) of aromatic halides with arylboronic acids.

TABLE 1
Suzuki coupling of aromatic halides with arylboronic acids
| No. | Halide A | Boronic acid B | Product C | Catalyst K [ppm] | Method | Time [h] | Yield [%] |
|---|---|---|---|---|---|---|---|
| 1 | 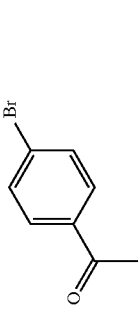 A1 | 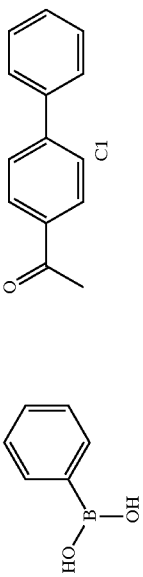 B1 |  C1 | 5 (K1–K14) | X1 | 1 | >99 |
| 2 | 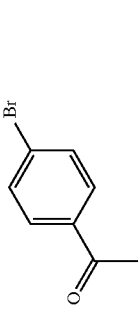 A1 | 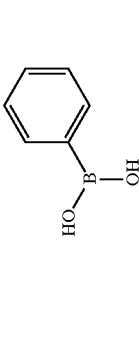 B2 | 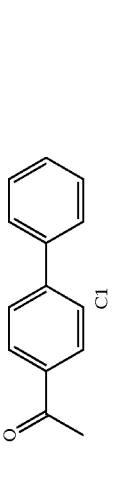 C2 | 5 (K1–K14) | X1 | 1 | 87 |
| 3 | 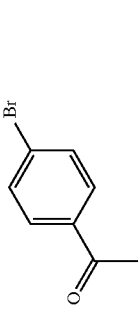 A1 | 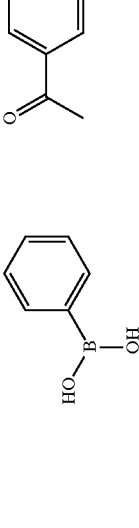 B3 |  C3 | 10 (K1–K14)<br>3 (K1–K14) | X1<br>X1 | 1.6<br>12 | >99<br>96 |
| 4 | 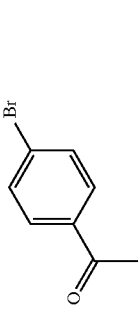 A1 |  B4 |  C4 | 30 (K1–K14)<br>3 (K1–K14) | X1<br>X1 | 2<br>2 | >99<br>60 |
| 5 | 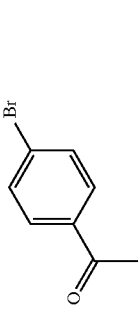 A1 | 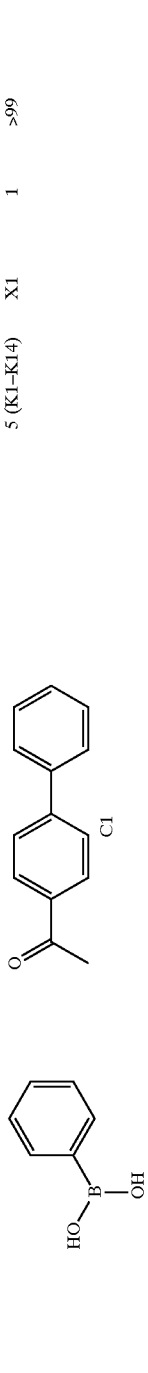 B5 |  C5 | 100 (K1–K14) | X1 | 16 | 66 |

TABLE 1-continued

Suzuki coupling of aromatic halides with arylboronic acids

| No. | Halide A | Boronic acid B | Product C | Catalyst K [ppm] | Method | Time [h] | Yield [%] |
|---|---|---|---|---|---|---|---|
| 6 | A1 (4-bromoacetophenone) | B6 (4-methylphenylboronic acid) | C6 | 30 (K1–K14) | X1 | 7 | 90 |
| 7 | A1 | B7 (3-methoxyphenylboronic acid) | C7 | 5 (K1–K14) | X1 | 2 | 97 |
| 8 | A1 | B8 (4-methoxyphenylboronic acid) | C8 | 5 (K1–K14) | X1 | 1 | >99 |
| 9 | A1 | B9 (4-methylthiophenylboronic acid) | C9 | 100 (K1–K14) | X1 | 16 | 82 |
| 10 | A1 | B10 (2-naphthylboronic acid) | | 30 (K1–K14) / 5 (K1–K14) | X1 / X1 | 1 / 4 | 94 / 53 |

TABLE 1-continued

Suzuki coupling of aromatic halides with arylboronic acids

| No. | Halide A | Boronic acid B | Product C | Catalyst K [ppm] | Method | Time [h] | Yield [%] |
|---|---|---|---|---|---|---|---|
| 11 | A1 (4-bromoacetophenone) | B11 (4-vinylphenylboronic acid) | C11 | 100 (K1–K14) / 30 (K1–K14) | X1 / X1 | 1 / 4 | 96 / 53 |
| 12 | A2 (3-bromoanisole) | B1 (phenylboronic acid) | C12 | 30 (K1–K14) | X1 | 1 | >99 |
| 13 | A2 | B2 (3-chlorophenylboronic acid) | C13 | 30 (K1–K14) | X1 | 1 | 93 |
| 14 | A2 | B3 (4-chlorophenylboronic acid) | C14 | 30 (K1–K14) | X1 | 1 | 89 |
| 15 | A2 | B4 (4-fluorophenylboronic acid) | C15 | 30 (K1–K14) | X1 | 2.5 | 91 |

TABLE 1-continued

Suzuki coupling of aromatic halides with arylboronic acids

| No. | Halide A | Boronic acid B | Product C | Catalyst K [ppm] | Method | Time [h] | Yield [%] |
|---|---|---|---|---|---|---|---|
| 16 | A2 (3-Br, 4-MeO-C6H3) | B6 (4-Me-C6H4-B(OH)2) | C16 | 100 (K1–K14) | X1 | 16 | 96 |
| 17 | A2 | B7 (3-MeO-C6H4-B(OH)2) | C17 | 30 (K1–K14) | X1 | 1 | 97 |
| 18 | A2 | B8 (4-MeO-C6H4-B(OH)2) | C18 | 30 (K1–K14) | X1 | 3 | 70 |
| 19 | A2 | B10 (2-naphthyl-B(OH)2) | C19 | 30 (K1–K14) | X1 | 4 | 81 |

TABLE 1-continued

Suzuki coupling of aromatic halides with arylboronic acids

| No. | Halide A | Boronic acid B | Product C | Catalyst K [ppm] | Method | Time [h] | Yield [%] |
|---|---|---|---|---|---|---|---|
| 20 | A2 (3-MeO-bromobenzene) | B11 (4-vinylphenylboronic acid) | C20 (3-methoxy-4'-vinylbiphenyl) | 1000 (K1–K14) | X1 | 1 | 90 |
| 21 | A4 (2-bromomesitylene) | B3 (4-chlorophenylboronic acid) | C21 (4'-chloro-2,4,6-trimethylbiphenyl) | 100 (K1–K14) | X1 | 1 | 97 |
| 22 | (2-bromonitrobenzene) | B1 (phenylboronic acid) | C22 (2-nitrobiphenyl) | 30 (K1–K14)<br>100 (K1–K14) | X1<br>X1 | 4<br>2 | 88<br>>99 |
| 23 | A5 (4'-chloroacetophenone) | B1 (phenylboronic acid) | C1 (4-acetylbiphenyl) | 100 (K1–K11) | X2 | 1 | >99 |
| 24 | A6 (3-MeO-chlorobenzene) | B1 (phenylboronic acid) | C12 (3-methoxybiphenyl) | 1000 (K1–K11) | X2 | 3 | 94 |

TABLE 1-continued
Suzuki coupling of aromatic halides with arylboronic acids
| No. | Halide A | Boronic acid B | Product C | Catalyst K [ppm] | Method | Time [h] | Yield [%] |
|-----|----------|----------------|-----------|-------------------|--------|----------|-----------|
| 25 | 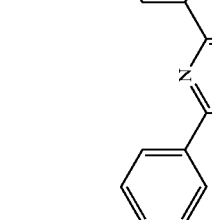 A7 | 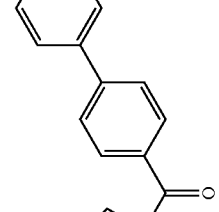 B1 | 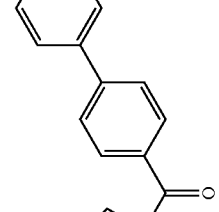 C23 | 5000 (K1–K6) | X1 | 18 | 84 (isolated) |
| 26 | 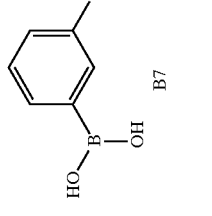 A8 | 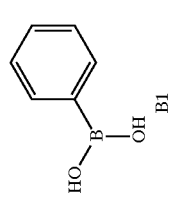 B7 | 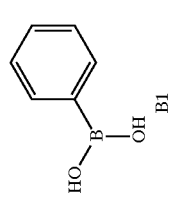 C24 | 500 000 (K1–K6) | X2 | 3 | 82 (isolated) |

All aryl halides A used, with the exception of A6 and A7, and boronic acids B are commercially available (for example from Acros, Aldrich, Alfa, Avocado, Fluka, Lancaster or Riedelde Haën) and can be used without prior purification. The solvents xylene (isomeric mixture, Fluka) and dimethoxyethane (Fluka) are to be dried before use by letting them stand over molecular sieve 4 Å. $K_2CO_3$ and $Cs_2CO_3$ are used in dry form, supplied by Fluka. The analytical data of the products C either correspond to the data described in the literature or are provided in:

C1 (*J. Chem. Soc. Perkin Trans.* 2, 1984, 771).
C2 (*Tetrahedron*, 1994, 50, 8301).
C3 (*J. Org. Chem.*, 1980, 45, 441).
C4 (*Mol. Cryst. Liq. Cryst.*, 1991, 200, 109).
C5 (*Med. Promst. SSR*, 1965, 17, 13; *Chem. Abstr.* 1963, 59, 12693, *Chem. Abstr.* 1972, 77, 19386).
C6 (*Mol. Cryst Liq. Cryst.*, 1991, 200, 109).
C7 (*J. Am. Chem. Soc.*, 1954, 76, 2357; ibid 1954, 76, 2361; *Tetrahedron*, 1994, 50, 8301).
C8 (*Tetrahedron*, 1985, 41, 5619; *Mol. Cryst Liq. Cryst.*, 1991, 200, 109; *J. Org. Chem.*, 1993, 58, 5434).
C9 (*J. Med. Chem.*, 1983, 26, 1196)
C10 analytical data: (purity>99% GC); molecular mass $C_{18}H_{14}O$: 246.31; calcd. C: 87.78%, H: 5.73%; found C: 87.52%, H: 5.80%.
This compound has already been described, but without indication of analytical data: (*Tetrahedron Lett.*, 1993, 34, 4019; *Russ. J. Org. Chem.*, 1994, 30, 827).
C11 analytical data: (purity>99% GC); molecular mass $C_{16}H_{14}O$: 222.29; calcd. C: 86.45%, H: 6.35%; found C: 86.31%, H: 6.19%.
C12 (see Example 1.1).
C13 analytical data: (purity>99% GC); molecular mass $C_{13}H_{11}OCl$: 218.68; calcd. C: 71.40%, H: 5.07%; found C: 71.58%, H: 5.05%.
C14 (*Bull. Chem. Soc. Jpn.*, 1963, 980; ibid, 1963, 982; *Biomed. Mass Spectrom.*, 1977, 310; *Can. J. Chem.*, 1982, 60, 990).
C15 (*Z. Naturforsch. B Anorg. Chem. Org. Chem.*, 1983, 38, 226; *J. Org. Chem.*, 1989, 54, 4844; *Spectrochim. Acta Part A*, 1981, 37, 689).
C16 (*Tetrahedron*, 1994, 50, 8301).
C17 (*Tetrahedron*, 1970, 26, 4041; *Phosphorous, Sulfur Silicon Relat. Elem.*, 1994, 92, 231; *Magn. Reson. Chem.*, 1986, 24, 81).
C18 (*Helv. Chim. Acta*, 1988, 71, 1199).
C19 (*J. Chem. Soc. Perkin Trans* 1, 1973, 1451; ibid, 1973, 1454).
C20 analytical data: (purity>99% GC); molecular mass $C_{15}H_{14}O$: 246.31; calcd. C: 85.68%, H: 6.71%; found C: 85.74%, H: 6.59%.
C21 (*Chem. Ber.*, 1978, 111, 1323; *J Org. Chem.*, 1984, 9, 1594).
C22 (*Tetrahedron Lett.*, 1995, 36, 6567; *Bull. Chem. Soc. Jpn.*, 1995, 68, 1701).
C23 (see Example 2).
C24 (see Example 3).

Example 1 (example of method X1)

1.1

Suzuki coupling of an aryl bromide with a phenylboronic acid using the catalysts K1–K14 (see Table 1, No. 12, method X1):

30 ppm (0.0018 9 mmol) each of the catalysts K1 to K14 (1.2), 16.3 g of $K_2CO_3$ (117.6 mmol) and 10.8 g of phenylboronic acid B1 (88.3 mmol) are added to a solution of 11.0 g of 3-bromoanisol A2 (58.8$x_1$) in 110 ml of xylene. The reaction mixture is refluxed for 60 minutes. GC analysis (reaction: 100%, yield: 3-methoxybiphenyl C12>99%). The mixture is worked up in water and the solvent is evaporated. 3-Methoxybiphenyl C12 is isolated without any further purification (yield:>95%, purity:>99% GC). $^1$H—NMR-identical with the described data (*J. Chem. Soc. Perkin Trans.* 1, 1972,1304; ibid. 1306). Molecular mass $C_{13}H_{11}O$: 183.23; cald. C. 85.22%, H: 6.05%; found C: 85.31%, H: 6.08%.

1.2

μ-Halo-phosphine ($\eta^3$-allyl)palladium(II) catalysts used.

1.2.1

K 1: μ-Chloro(tricyclohexylphosphine)($\eta^3$-allyl)palladium (II). The preparation is described in G. M. Direnzo et al. *J. Am. Chem. Soc.* 1996, 118, 6225, or H. Lehmkuhl and V. Dimitrov *J. Organomet. Chem.* 1996, 519, 83).

1.2.2.1

K 2: μChloro(tdisopropylphosphine)($\eta^3$-allyl)palladium(II). 23.2 g (63.37 mmol) of di-μ-chloro($\eta^3$-2-allyl) dipalladium(II) are dissolved in 500 ml of dry THF at room temperature under argon. 27 ml (140 mmol) of triisopropylphosphine are slowly added to the stirred yellow solution and the resulting lemon yellow solution is then stirred for 3 hours at room temperature. The solution is filtered and concentrated to a volume of about 50 ml. After adding 300 ml of dry hexane, the product precipitates as a yellow solid. The precipitate is collected by filtration and dried in vacuo, giving a yellow powder; yield: 41.8 g (96%).

Molecular mass $C_{12}H_{26}PPdCl$; 343.17; calcd. C: 42.00%, H: 7.64%, P: 8.97%, Pd: 31.01%; found C: 41.88%; H: 7.68%, P: 8.85%, Pd: 31.29%;

$^{31}$P-NMR (101 MHz, CDCl$_3$): δ=53.36 (s).

1.2.2.2

The preparation of the dimeric di-μ-chloro($\eta^3$-2-allyl) dipalladium(II) is carried out in accordance with Y. Tatsuno et al., *Inorg. Synth.* 1979, 14, 220.

1.2.3

K 3: μ-Bromo(tricyclohexylphosphine)($\eta^3$allyl)palladium (II). The preparation is described in T. Yamamoto et al. *Organometallics*, 1986, 5, 1559.

1.2.4.1

K 4: μBromo(triisopropylphosphine)($\eta^3$-allyl)palladium(II). In analogy to the preparation of K 2 (1.2.2.1), 28.82 g (63.37 mmol) of di-μ-bromo(η3-2-allyl)dipalladium(II) are reacted with 26.7 ml (140 mmol) of trisopropylphosphine. The precipitate is collected by filtration and dried in vacuo, giving a yellow powder; yield: 40.29 g (82%).
Molecular mass $C_{12}H_{26}PPdBr$: 387.64; calcd. C: 37.18%, H: 6.76%, P: 7.99%, Pd: 27.45%; found C: 37.25%, H: 6.74%, P: 8.01%; Pd: 27.47%;
$^{31}P$-NMR (101 MHz, $CDCl_3$): δ=52.87 (s).
1.2.4.2

The preparation of the dimeric di-μ-bromo($\eta^3$-2-allyl) dipalladium(II) is carried out in accordance with Y.Inoue et al. *Synthesis*, 1984, 3, 244.
1.2.5.1

K 5: μ-Iodo(tricyclohexylphosphine)($\eta^3$-allyl)palladium(II). In analogy to the preparation of K 2 (1.2.2.1), 10.2 g (18.6 mmol) of di-μ-iodo($\eta^3$-2-allyl)dipalladium(II) are reacted with 11.5 g (40.9 mmol) of tricyclohexylphosphine. The precipitate is collected by filtration and dried in vacuo, giving a yellow powder; yield: 18.6 g (90%);
molecular mass $C_{21}H_{38}PPdI$: 554.83; calcd. C: 45.46%, H: 6.90%, P: 5.58%, Pd: 19.18%; found C: 45.53%, H: 6.01%, P: 5.45%; Pd: 19.21%;
$^{31}$-NMR (101 MHz, $CDCl_3$): δ=40.52 (s).
1.2.5.2

The preparation of di-μ-iodo($\eta^3$-2allyl)dipalladium(II) is carried out in accordance with Y.Inoue et al. *loc. cit.*
1.2.6

K 6: μ-Iodo(tri-isopropylphosphine)($\eta^3$-allyl)palladium(II). In analogy to the preparation of K 2 (1.2.2.1), 15.7 g (28.6 mmol) of di-μ-iodo($\eta^3$-2-allyl)dipalladium(II) are reacted with 12.0 ml (62.9 mmol) of triisopropylphosphine. The precipitate is collected by filtration and dried in vacua, giving a yellow powder; yield: 17.9 g (72%);
molecular mass $C_{12}H_{26}PPdI$: 434.64; calcd. C: 33.16%, H: 6.03%, P: 7.13%, Pd: 24.48%; found C: 33.15%, H: 6.00%, P: 7.18%, Pd: 24.44%; $^{31}P$-NMR (101 MHz, $CDCl_3$); δ=52.90 (s).
1.2.7.1

K 7: μ-Chloro(tricyclohexylphosphine)($^3$-1-phenylpropenyl)palladium(II). In analogy to the preparation of K 2 (1.2.2.1), 518 mg (1.0 mmol) of di-μ-chloro ($\eta^3$-1-phenylpropenyl)dipalladium(II) are reacted with 617 mg (2.2 mmol) of tricyclohexylphosphine. The precipitate is collected by filtration, dried in vacuo, dissolved in dichloromethane and filtered through silica gel. Evaporation of the solvent and drying of the solid in vacuo gives a yellow powder; yield: 734 mg (68%);
molecular mass $C_{27}H_{42}PPdI$: 539.46; calcd. C: 60.12%, H: 7.85%, P: 5.74%, Pd: 19.72%; found C: 60.18%, H: 7.80%, P: 5.65%, Pd: 19.93;
$^{31}$-NMR (101 MHz, $CDCl_3$): δ=46.05 (s).
1.2.7.2

The preparation of the dimeric di-μ-chloro($\eta^3$-1-phenylpropenyl)dipalladium(II) is carried out in accordance with A. Goliaszewski and J. Schwarz *Tetrahedron* 1985, 41, 5779.
1.2.8

K 8: μ-Chloro(tricyclohexylphosphine)($\eta^3$-3-methylbutenyl)palladium(II). The preparation is described in B. Åkermark et al. *Organometallics* 1987, 6, 620.
1.2.9.1

K 9: μ-Chloro(tricyclohexylphosphine)(6,6-dimethyl-2,3,10-$\eta^3$-2mathylenebicyclo-[3.1.1]-heptyl)palladium(II). In analogy to the preparation of K 2 (1.2.2.1), 3.31g (5.97mmol) of di-μ-chloro(6,6-dimethyl-2,3,10-$\eta^3$-2-methylenebicyclo[3. 1.1 ]heptyl)dipalladium(II) are reacted with 3.68 g (13.13 mmol) of tricyclohexylphosphine, giving an orange, elastic mass; yield: 5.86 g (88%);
molecular mass $C_{28}H_{48}PPdCl$: 557.52 ; calcd. C: 60.32%, H: 8.68%, P: 5.56%, Pd: 19.09%; found C: 59.99%, H: 8.61%, P: 5.35%, Pd: 19.25%;
$^{31}P$-NMR (101 MHz, $CDCl_3$); δ=25.71 (s).
1.2.9.2

The preparation of the dimeric di-μ-chloro(6,6-dimethyl-2,3,10-$\eta^3$-2-methylenebicyclo-[3.1.1.]heptyl)dipalladium (II) is carried out in accordance with B. M. Trost et al. *J. Amer. Chem. Soc.* 1980, 102, 3572; ibid. 1978, 100, 3407.
1.2.10.1

K 10: μ-Chloro(tricyclohexylphosphine)($\eta^3$-2-chloropropenyl)palladium(II). In analogy to the preparation of K 2 (1.2.2.1), 8.73 g (20.1 mmol) of di-μ-chloro ($\eta^3$-2-chloropropenyl)dipalladium(II) are reacted with 12.39 g (44.2 mmol) of tricyclohexylphosphine. The precipitate is collected by filtration and dried in vacuo, giving an orange powder; yield: 17.4 g (87%);
molecular mass $C_{21}H_{37}PPdCl_2$: 497.80; calcd. C: 50.67%, H: 7.49%, P: 6.22%, Pd: 21.37%; found C: 50.70%, H: 7.45%, P: 6.14%, Pd: 21.46%;
$^{31}P$-NMR (101 mHz, $CDCl_3$); δ=59.13 (s).
1.2.10.2

The preparation of the dimeric di-μ-chloro($\eta^3$-2-chloropropenyl)dipalladium(II) is carried out in accordance with J.-E. Bäckvall et al. *Organometallics* 1997, 16,1058.
1.2.11

K 11: μ-Trichlorotin(tricyclohexylphosphine)($\eta^3$-allyl) palladium(II). The preparation is carried out as described in M. Gianotti et al. *Inorg. Chimica Acta* 1987, 133, 255:
μ-Chloro(tricyclohexylphosphine)($\eta^3$-allyl)palladium(II) (324 mg, 0.7 mmol) is dissolved in dry dichloromethane (20 ml) under argon. Tin(II)chloride is added to the stirred yellow solution. The resulting suspension is stirred for another 2 hours at room temperature. After evaporating the solvent, a faintly yellow powder is obtained, yield; 330 mg (72%).
Molecular mass $C_{21}H_{38}PPdSnCl_3$: 653.00; calcd. C: 38.63%, H: 5.87%, P: 4.74%, Pd: 16.29%; found C: 38.55%, H: 5.88%, P: 4.61%, Pd: 15.98%;
$^{31}P$—NMR (101 mHz, $CDCl_3$); δ=41.14 (s).

K12: Dichloro($\eta^3$-allyl)(tetraphenylphosphonium)palladate
The preparation is described in R. J. Goodfellow et al., *J. Chem. Soc.* (A), 196 784.

K13: Dibromo(η3-allyl)(tetraphenylphosphonium)palladate
The preparation is described in R. J. Goodfellow et al., *J. Chem. Soc.* (A), 1966, 784.

K14: Diiodo ($\eta^3$-allyl)(tetraphenylphosphonium)palladate
The preparation is carried out in analogy to R. J. Goodfellow et al., *J. Chem. Soc.* (A), 1966, 784:

20 ml of $H_2O$ are added under argon to 595 mg (1.08 mmol) of di-μ-iodo($\eta^3$-2-allyl)dipalladium(II) and 720 mg (4.34 mmol) of potassium iodide. The stirred suspension is heated for 30 minutes to 60° C. 1.04 g (2.22 mmol) of tetraphenylphosphonium iodide are added to the resulting orange solution which is then cooled to room temperature. The mixture is extracted with dichloromethane (3×10 ml) and the combined extracts are dried with magnesium sulfate. Filtration and removal of the solvent by distillation gives an orange powder, yield: 1.58 g (99%).
Molecular mass $C_{27}H_{25}PPdI_2$: 740.70; calcd. C: 43.78%, H: 3.40%, P: 4.18%, Pd: 14.37%; found C: 43.97%, H: 3.50%, P: 4.31%, Pd: 13.98%; $^{31}P$-NMR (101 mHz, $CDCl_3$); δ=23.73 (t).

Example 2 (Example of Method X1)

Synthesis of a photoinitiator by Suzuki coupling using the catalysts K1–K6 (see Table 1, No. 24):

A solution of 3.18 g (8.83 mmol) of 2-benzyl-1-(4-bromophenyl)-2-dimethylaminobutan-1-one A7 in 300 ml of dimethoxyethane is charged with 0.044 mmol each of the catalysts K1–K6 (1.2), 1.0 ml of a 2N aqueous $Cs_2CO_3$ solution and 1.51 g (12.36 mmol) of phenylboronic acid B1. This reaction mixture is heated for 18 hours under reflux conditions. GC analysis (reaction: 100%, yield: 2-benzyl-1-biphenyl-4-yl-2-dimethylaminobutan-1-one C23: 85%). The mixture is worked up in water and filtered through silica gel; yield: 84%; molecular mass $C_{25}H_{27}NO$: 357.50; calcd. C: 83.99%, H: 7.61%, N: 3.92%; found C: 84.05%; H: 7.60%, N: 3.81%.

Example 3 (Example of Method X2)

Suzuki coupling of an aryl chloride with a phenylboronic acid using the catalysts K1–K11 (see Table 1, No. 24, method )(X2):

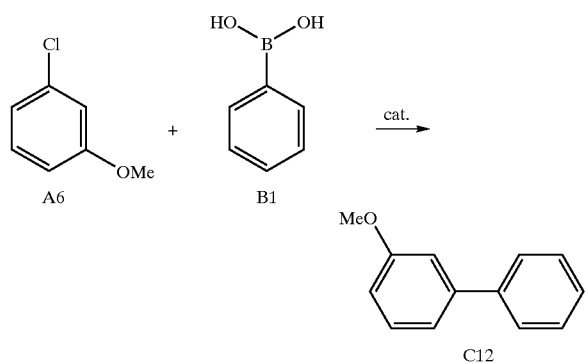

A solution of 8.34 g of 3-chloroanisol A6 (58.8 mmol) in 110 ml of xylene is charged with 1000 ppm (0.059 mmol) each of the catalysts K1 to K11 (1.2), 16.3 g of $K_2CO_3$ (117.6 mmol) and 10.8 g of phenylboronic acid B1 (88.3 mmol). The reaction mixture is refluxed for 60 minutes. GC analysis (reaction 95%, yield 3-methoxybiphenyl C2>94%). The mixture is worked up in water and the solvent is evaporated. 3-Methoxybiphenyl C12 (yield:>95%, purity:>99% GO) is isolated without any further purification. $^1$H-NMR-identical with the described data (*J. Chem. Soc. Perkin Trans.* 1, 1972, 1304; ibid. 1306). Molecular mass $C_{13}H_{11}O$: 183.23; calcd. C: 85.22%, H: 6.05%; found C: 85.31%, H: 6.08%.

Example 4 (Additional Example of Method X2)

Synthesis of a UV absorber by Suzuki coupling, using the catalysts K1–K6 (see Table 1, No.25):

A solution of 220 mg (0.44 mmol) of 2-(4,6-bis-4-chlorophenyl)-[1,3,5]triazin-2-yl-5-hexyloxyphenol A7 in 20 ml of dimethoxyethane is charged with 0.0025 mmol each of the catalysts K1–K6 (1.2), 0.5 ml of a 2N aqueous $Cs_2CO_3$ solution and 213 mg (1.4 mmol) of methoxy phenylboronic acid B7, and the reaction mixture is heated for 3 hours under reflux conditions. DC analysis (reaction>95%). The mixture is worked up in water and filtered through silica gel; yield 2-[4,6-bis-(3'-methoxybiphenyl-4-yl)-[1,3,5] triazin-2-yl]-5-hexyloxyphenol C24: 82%; molecular mass $C_{41}H_{39}N_3O$: 637.79; calcd. C: 77.21%, H: 6.16%, N: 2.20%; found C: 77.15%, H: 6.09%, N: 2.15%.

TABLE 2

Heck coupling of aromatic halides with olefins

| No. | Halide A | Olefin D | Product C | Catalyst K [ppm] | Method | Time [h] | Yield [%] |
|---|---|---|---|---|---|---|---|
| 1 | A1 (4-acetyl bromobenzene) | D1 (butyl acrylate) | C25 | 5 (K1–K11) | Y | 1.5 | >99 |
| 2 | A5 (4-acetyl chlorobenzene) | D1 | C25 | 36 000 (K1–K11) | Y | 6 | 55 |
| 3 | A2 (3-methoxy bromobenzene) | D1 | C26 | 10 000 (K1–K11) | Y | 24 | 90 |

TABLE 2-continued

Heck coupling of aromatic halides with olefins

| No. | Halide A | Olefin D | Product C | Catalyst K [ppm] | Method | Time [h] | Yield [%] |
|---|---|---|---|---|---|---|---|
| 4 | 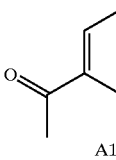 A1 | 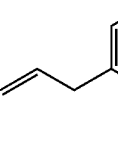 D2 | 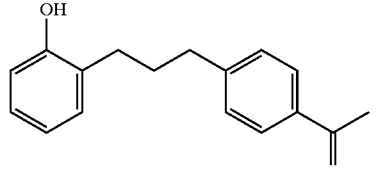 C27 | 10 000 (K1–K11) | Y | | 80 (isolated) |

All aryl halides A and olefins D used are commercially available (for example from Acros, Aldrich, Alfa, Avocado, Fluka, Lancaster or Riedel-de Haën) and can be used without any prior purification. The solvent dimethylformamide (Fluka) is to be dried before use by letting it stand over molecular sieve 4 Å. NaOAc can be obtained and used in dry form from Fluka. The analytical data of the products C either correspond to the data described in the literature or are provided in:

C25 (see Example 4).
C26 (*J. Chem. Soc. Perkin Trans.* 1, 1990, 2207).
C27 analytical data: (purity>99% GC); molecular mass $C_{17}H_{16}O$: 252,31; calcd. C: 80.93%, H: 6.39%; found C: 80.81%, H: 6.41%.

Example 5 (Example of Method Y)

Heck coupling of aryl bromide with acrylate using the catalysts K1–K11:

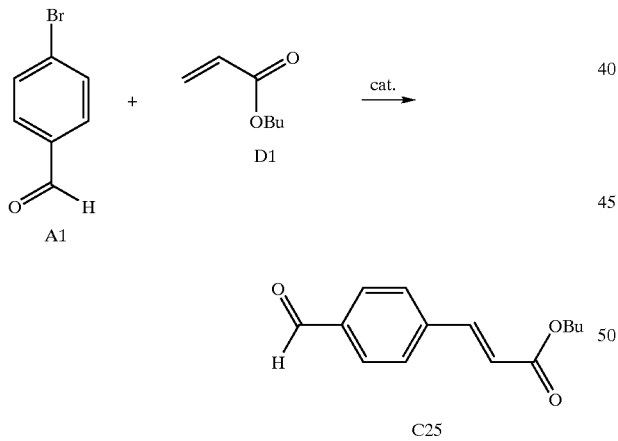

20.4 g (110 mmol) of 4-bromobenzaldehyde A1, 19.7 g (154 mmol) of nbutylacrylate D1, 10 mg (0.05 mmol) of 2,6-di- tert-butylphenol and 9.9 g (120 mmol) of sodium acetate are mixed with 200 ml of dimethylacetamide and, after adding 5 ppm each of the catalysts K1–K11 (1.2), are stirred for 90 minutes at 190° C. in an oil bath. The mixture is worked up in water and extracted with ether. The organic phases are washed several times with water and are filtered through silica gel. The solvent is evaporated, giving 4-formylcinnamic acid-n-butyl ester C25 (purity>99% GC) without any purification in a yield of >95%. Analytical data identical with the described data (J. Organomet. Chem, 1995, 491, 1–2, C1; *Angew. Chem.*, 1995, 107, 1989). Molecular mass $C_{14}H_{16}O_3$: 232.28; calcd. C: 72.39%, H: 6.94%; found C: 72.46%, H: 7.00%.

What is claimed is:

1. A process for the preparation of a biphenyl of formula

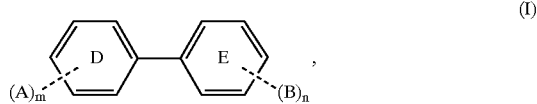

(I)

wherein A and B define substituents; m and n define integers from 0 to 5 and the number of substituents at the phenyl radicals D and E; or of an aromatic olefin of formula

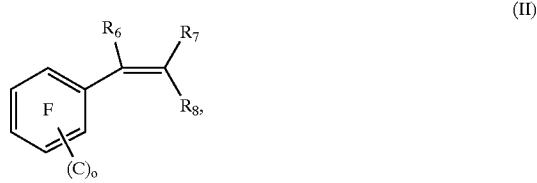

(II)

wherein C defines substituents, o defines integers from 0 to 5 and the number of substituents at the phenyl radical F, and $R_6$, $R_7$ and $R_8$ are hydrogen or substituents, which process comprises a) subjecting a phenyl derivative of formula

(III a)

(III b)

wherein A, B, m and n have the meanings cited for formula I and X is a leaving group, for the preparation of the biphenyl (I) to a coupling reaction with an arylboronic acid derivative of formula

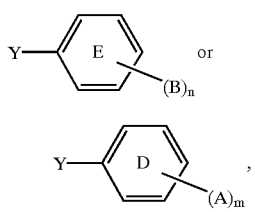

wherein A, B, m and n have the meanings cited for formula I and Y is the —B(OH)$_2$ group or mono- or diester derivatives of —B(OH)$_2$; and b) subjecting a phenyl derivative of formula

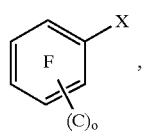

wherein C and o have the meanings cited for formula II and X is a leaving group, for the preparation of the aromatic olefin (II) to a coupling reaction with an olefin of formula

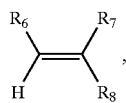

wherein R$_6$, R$_7$ and R$_8$ have the meanings cited for formula II, each in the presence of a catalytically effective amount of an olefinic palladium complex compound of formula

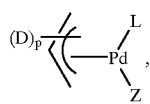

wherein L is a neutral ligand having electron-donor properties, Z is an anionic ligand and D is a substituent, and p is an integer from 0 to 5 and defines the number of substituents at the allyl group; or a') subjecting a phenyl derivative (III a) or (IIIb), wherein A, B, m and n have the meanings cited for formula I and X is chloro, bromo or iodo, for the preparation of the biphenyl (I) to a coupling reaction with an arylboronic acid derivative (IV a) or (IV b), wherein A, B, m and n have the meanings cited for formula I and Y is the —B(OH)$_2$ group or mono- or diester derivatives of —B(OH)$_2$; or b') subjecting a phenyl derivative (V), wherein C and o have the meanings cited for formula II and X is bromo or iodo, for the preparation of the aromatic olefin (II) to a coupling reaction with an olefin (VI), wherein R$_6$, R$_7$ and R$_8$ have the meanings cited for formula II, each in the presence of a catalytically effective amount of an olefinic ionic palladium complex compound of formula

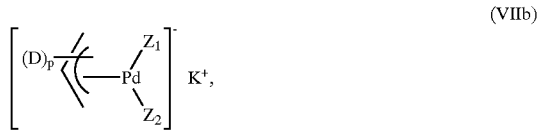

wherein Z$_1$ and Z$_2$ are anionic ligands and K$^+$ is a non-coordinating cation, and D and p have the cited meanings, and isolating the biphenyl (I) or the condensed aromatic olefin (II) after the completion of the process variants a), b), a') or b').

2. A process according to claim 1, wherein the structures of the substituents A, B and C and R$_6$–R$_8$ in the starting materials of formulae III a, III b, IV a, IV b and V remain unchanged under the conditions of the coupling reactions.

3. A process according to claim 1, wherein the structures of the substituents D in the olefinic palladium complex compound (VII a) and in the olefinic ionic palladium complex compound (VIII b) remain unchanged under the conditions of the coupling reaction.

4. A process according to claim 1 for the preparation of a) a biphenyl (I) or b) an aromatic olefin (II), which comprises a) subjecting a phenyl derivative (III) for the preparation of the biphenyl (I) to a coupling reaction with an arylboronic acid derivative (IV); or b) subjecting a phenyl derivative (V) for the preparation of the aromatic olefin (II) to a coupling reaction with an olefin (VI), each in the presence of an olefinic palladium complex compound (VII a), wherein L is a neutral ligand having electron-donor properties, Z is halogen and p is 0, or in the presence of an olefinic ionic palladium complex compound (VII b), wherein Z$_1$ and Z$_2$ are halogen, K$^+$ is the tetraphenylphosphonium cation and p is 0 and, after carrying out the process variants a) or b), isolating the biphenyls (I) or the condensed aromatic olefin (II).

5. A process according to claim 4 for the preparation of a) a biphenyl (I) or b) an aromatic olefin (II), which comprises carrying out the coupling reactions in each case in the presence of an olefinic palladium complex compound (VII a), wherein L is triisopropylphosphine or tricyclohexylphosphine, Z is halogen and p is 0.

6. A process according to claim 1 for the preparation of a) a biphenyl (I), wherein m and n are integers from 1 to 5, A is substituents from the group R$_1$, R$_2$, R$_3$, R$_4$ and R$_5$ which are selected from the group consisting of the functional groups or derivatised functional groups consisting of amino, C$_1$–C$_4$alkylamino, C$_1$–C$_4$dialkylamino, hydroxy, oxo, thio, —NO$_2$, carboxy, carbamoyl, sulfo, sulfamoyl, ammonio, amidino, cyano, formylamino, formamido and halogen, or are saturated or unsaturated aliphatic, cycloaliphatic or heterocycloaliphatic radicals, carbocyclic or heterocyclic aryl radicals, condensed carbocyclic, heterocyclic or carbocyclic-heterocyclic radicals, which may in turn be combined with any others of these radicals and which may be substituted by the cited functional groups or derivatised functional groups and which may in addition be interrupted by one or more than one bivalent radical from the group —O—, —S—, —C(=O)—O—, —O—C(=O)—, —C(=O)—N(C$_1$–C$_4$alkyl)—, —N(C$_1$–$_4$alkyl)—C(=O)—, —S(=O)—, —S(=O)$_2$—, S(=O)—O—, —S(=O)$_2$13 O—, —O——S(=O)—, —O—S(=O)$_2$—, —S(=O)—N(C$_1$–C$_4$alkyl)—, —S(=O)$_2$—N(C$_1$–C$_4$alkyl)—, —(C$_1$–C$_4$alkyl)N—S(=O)—, —(C$_1$–C$_4$alkyl)N—S(=O)$_2$—, —P(=O)—, —P(=O)—O—, —O—P(=O)— and —O—P(=O)—O—, and wherein two substituents from the group R$_1$, R$_2$, R$_3$, R$_4$ and R$_5$ can also be bivalent, bridge-like C$_2$–C$_6$alkylene, C$_4$–C$_8$alkyldiylidene or C$_4$–C$_8$alkenyidiylidene groups, which are bound to the phenyl ring D or to the heteroaryl substituent A or which are condensed to an aromatic bicycle, which can likewise be substituted by the cited functional groups or substituents; and B is substituents from the group R$_6$, R$_7$, R$_8$, R$_9$ and R$_{10}$ which are as defined under A for R$_1$ to R$_5$; or b) an aromatic olefin (II), wherein o is an integer from 1 to 5 and C is 1 to 5 substituents from the group R$_1$, R$_2$, R$_3$, R$_4$ and R$_5$ which are as defined under A for R$_1$ to R$_5$ and wherein R$_6$, R$_7$ and R$_8$ in the olefinic side chain are hydrogen or are as defined under A for R$_1$ to R$_5$, which process comprises carrying out the process variant a) for the preparation of the biphenyl (I) and the process variant b) for the preparation of the aromatic olefin (II), each in the presence of an olefinic palladium complex compound (VII a) or of an olefinic ionic palladium complex compound (VII b).

7. A process according to claim 6 for the preparation of
a) a biphenyl (I), wherein m and n are integers from 1 to 5, A is substituents from the group R$_1$, R$_2$, R$_3$, R$_4$ and R$_5$, which are each independently of one another functional groups from the group consisting of amino, C$_1$–C$_4$alkylamino, C$_1$–C$_4$dialkylamino, hydroxy, oxo, thio, —NO$_2$, carboxy and halogen, or substituents from the group consisting of C$_1$–C$_{20}$alkyl, C$_2$–C$_{20}$alkenyl, C$_2$–C$_{20}$alkynyl, C$_3$–C$_{12}$cycloalkyl, C$_7$–C$_{12}$bicycloalkyl, C$_4$–C$_{12}$-cycloalkenyl, C$_2$–C$_{11}$heterocycloalkyl, carbocyclic C$_6$–C$_{16}$aryl, C$_2$–C$_{15}$heteroaryl, carbocyclic C$_7$–C$_{16}$aralkyl and C$_2$–C$_{15}$heteroarylalkyl, which can in turn be substituted by the cited functional groups and which can be interrupted by bivalent radicals, and B is substituents from the group R$_6$, R$_7$, R$_8$, R$_9$ and R$_{10}$ which are as defined under A for R$_1$ to R$_5$; or b) an aromatic olefin (II), wherein o is an integer from 1 to 5 and C is 1 to 5 substituents from the group R$_1$, R$_2$, R$_3$, R$_4$ and R$_5$ which are as defined under A for R$_1$ to R$_5$ and wherein R$_6$, R$_7$ and R$_8$ in the olefinic side chain are hydrogen or are as defined under A for R$_1$ to R$_5$, which process comprises carrying out the process variant a) for the preparation of the biphenyl (I) and the process variant b) for the preparation of the aromatic olefins (II), each in the presence of an olefinic palladium complex compound (VII a) or of an olefinic ionic palladium complex compound (VII b).

8. A process according to claim 1, wherein according to variant a) the leaving group X in the phenyl derivative (III a) or (III b) is halogen or an organosulfonyl radical.

9. An olefinic palladium complex compound of formula

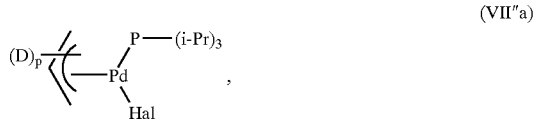

(VII″a)

wherein i-Pr is isopropyl, Hal is chloro or bromo and D is substituents, and p is an integer from 0 to 5 and defines the number of substituents at the allyl group.

* * * * *

UNITED STATES PATENT AND TRADEMARK OFFICE
CERTIFICATE OF CORRECTION

PATENT NO.      : 6,417,357 B1
DATED           : July 9, 2002
INVENTOR(S)     : Michael Tinkl et al.

It is certified that error appears in the above-identified patent and that said Letters Patent is hereby corrected as shown below:

<u>Title page,</u>
Item [86], should read
-- [86]  PCT No.:
         § 371 (c)(l),
         (2), (4) Date:  September 14, 2000 --.
Item [87], should read:
-- [87]  PCT Pub. No.:  WO 99/47474
         PCT Pub. Date: Sept. 23, 1999 --.

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,417,357 B1 Page 1 of 1
DATED : July 9, 2002
INVENTOR(S) : Michael Tinkl et al.

It is certified that error appears in the above-identified patent and that said Letters Patent is hereby corrected as shown below:

<u>Title page,</u>
Item(s) [86] and [87], should read as follows:
-- [86]  PCT No.:          PCT/EP99/01474
         § 371 (c)(l),
         (2), (4) Date:    September 14, 2000

[87]  PCT Pub. No.:     WO 99/47474
         PCT Pub. Date:    Sept. 23, 1999 --.

This certificate supersedes Certificate of Correction issued September 16, 2003.

Signed and Sealed this

Twenty-fifth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,417,357 B1  Page 1 of 1
DATED : July 9, 2002
INVENTOR(S) : Michael Tinkl et al.

It is certified that error appears in the above-identified patent and that said Letters Patent is hereby corrected as shown below:

<u>Title page,</u>
Item [22], should read:
-- [22] PCT Filed: March 8, 1999 --.

Signed and Sealed this

Twenty-fourth Day of February, 2004

JON W. DUDAS
*Acting Director of the United States Patent and Trademark Office*